United States Patent [19]

Koppes et al.

[11] Patent Number: 5,276,171
[45] Date of Patent: Jan. 4, 1994

[54] 2-AZIDO-2,2-DIFLUOROETHANOL

[75] Inventors: William M. Koppes, Adelphi; Michael Chaykovsky, Columbia, both of Md.

[73] Assignee: The United States of America as represented by the Secretary of the Navy, Washington, D.C.

[21] Appl. No.: 59,767

[22] Filed: May 10, 1993

[51] Int. Cl.$^5$ .............................................. C07C 69/76
[52] U.S. Cl. ...................................................... 552/10
[58] Field of Search ........................................... 552/10

[56] References Cited

U.S. PATENT DOCUMENTS 4,713,469 12/1987 Takeuchi et al. ...................... 552/10

Primary Examiner—Alan Siegel
Attorney, Agent, or Firm—John D. Lewis; Roger D. Johnson

[57] ABSTRACT

2-Azido-2,2-difluoroethanol is useful in the preparation of energetic plasticizers for explosives and propellants. Ethyl 2-bromo-2,2-difluoroacetate reacts with sodium azide to produce ethyl 2-azido-2,2-difluoroacetate which then reacts with sodium borohydride in water to produce the 2-azido-2,2-difluoroethanol.

1 Claim, No Drawings

2-AZIDO-2,2-DIFLUOROETHANOL

BACKGROUND OF THE INVENTION

This invention relates to alcohols and more particularly to energetic alcohols useful in the synthesis of energetic plasticizers for explosives and propellants.

Currently available energetic forms of ethanol include 2-azidoethanol, $N_3CH_2CH_2OH$; 2-flouro-2,2-dinitroethanol, $CF(NO_2)_2CH_2OH$; and 2,2,2-trinitroethanol, $C(NO_2)_3CH_2OH$. These are used to form various nitro(azido) aliphatic compounds useful in propellant and explosive formulations. Also of value in these applications are fluorinated alcohols such as 2,2,2-trifluoroethanol, $CF_3CH_2OH$; 2,2,3,3,3-heptafluoropropan-1-ol, $CF_3CF_2CH_2OH$, etc. The limitations of the prior art nitro, azido, and fluoro alcohols result from the low-density of the azidoethyl group, the tendency of nitroalkyl groups to increase melting points, and the lack of energetic groups in the fluoroalkyl groups.

It would be desirable to provide alcohols with a substituent group that would provide high density, high energy, a low melting point, and good thermal and shock stability.

SUMMARY OF THE INVENTION

Accordingly, an object of this invention is to provide a new energetic alcohol.

Another object of this invention is to provide a new energetic alcohol that is useful in the synthesis of energetic plasticizers and other components of propellants and explosives.

A further object of this invention is to provide a new energetic alcohol with good stability.

Yet another object of this invention is to provide a new energetic alcohol that can be used to produce new, stable, energetic plasticizers with low melting points.

These and other objects of this invention are accomplished by providing 2-azido-2,2-difluoroethanol, $N_3CF_2CH_2OH$.

DETAILED DESCRIPTION OF THE PREFERRED EMBODIMENT

This invention provides a new energetic alcohol 2-azido-2,2-difluoroethanol,

$N_3CF_2CH_2OH$, and a method of preparing it. 2-Azido-2,2-difluoroethanol is a new energetic alcohol which provides the physical properties of a fluoroalkanol in the construction of energetic molecules such as plasticizers and binders, while maintaining a high energy level due to the azide group. The 2-azido-2,2-difluoroethanol provides a means of coupling the 2-azido-2,2-difluoroethoxy group to energetic molecules. The fluorines provide stabilization of the azide group via C—N bond strengthening due to strong electron withdrawal effects. The effect on the physical properties by the addition of the 2-azido-2,2-difluoroethoxy group should be to lower melting point as with trifluoroethoxy, but with less diminution of energy and with the beneficial effect of lowering vapor pressure relative to fluoroalkyl groups. These features of 2-azido-2,2-difluoroethanol are advantageous in the synthesis of improved energetic plasticizers and polymeric binders. Two specific examples of utility would be the reaction of 2 moles of 2-azido-2,2-difluoroethanol and 1 mole of formaldehyde to produce bis(2-azido-2,2-difluoroethyl)formal, $H_2C(OCH_2CF_2N_3)_2$, or with one mole of acetaldehyde to produce bis(2-azido-2,2-difluoroethyl)acetal, $CH_3CH(OCH_2CF_2N_3)_2$.

The preparation of 2-azido-2,2-difluorethanol can be summarized as follow:

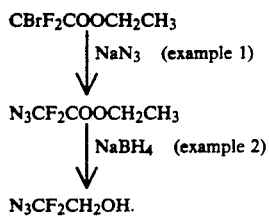

The ethyl 2-bromo-2,2-difluoroacetate, $CBrF_2COOCH_2CH_3$, starting material is available from chemical laboratory supply houses. The ethyl 2-bromo-2,2-difluoroacetate used in example 1 was obtained from PCR, Inc., P.O. Box 1466, Gainesville, Fla. 32602. The ethyl 2-bromo-2,2-difluoroacetate reacts with sodium azide, $NaN_3$, in dry dimethyl sulfoxide at room temperature (20° C.) to produce ethyl 2-azido-2,2-difluoroacetate, $N_3CF_2COOCH_2CH_3$. The reaction conditions are illustrated in example 1. Next, the ethyl 2-azido-2,2-difluoroacetate reacted with sodium borohydride, $NaBH_4$, in water to produce the desired 2-azido-2,2-difluoroethanol, $N_3CF_2CH_2OH$. The reaction conditions are illustrated in example 2. The reactivity of 2-azido-2,2-difluoroethanol is demonstrated by example 3 in which the alcohol reacts with phenylisocyanate.

The general nature of the invention having been set forth, the following examples are presented as specific illustrations thereof. It will be understood that the invention is not limited to these examples but is susceptible to various modifications that will be recognized by one of ordinary skill in the art.

Example 1

ETHYL 2-AZIDO-2,2-DIFLUOROACETATE

Powdered sodium azide (19.5 g, 0.3 mol) was added in portions, over 5 minutes, to a stirred solution of ethyl 2-bromo-2,2-difluoroacetate (50.74 g, 0.25 mol) in dry dimethyl sulfoxide (250 mL). After stirring at room temperature for 18 hours, the mixture was poured into water (750 mL) and extracted with methylene chloride (4×100 mL). The combined extracts were washed with water (4×100 mL), dried over anhydrous magnesium sulfate, then filtered, and the filtrate was distilled at atmospheric pressure through an indented (10 cm.) distillation column, at a bath temperature of 77° C., until no more methylene chloride distilled. $^1H$ NMR spectroscopy ($CDCl_3$; $(CH_3)_4Si$ internal standard) of the colorless residue showed a mixture of methylene chloride (31 mol %) and the azido ester (69 mol%); 4.53 (q, 2H, $CH_2$), 1.44 (t, 3H, $CH_3$). This corresponds to a yield of 34.44 g (83.4%) of the azido ester. The pure product was obtained as a colorless liquid by distillation under vacuum; bp 68° C./100 mm. $^{19}F$ NMR ($CDCl_3$, $CFCl_3$ internal standard) $\phi$ 84.8 (s). Anal. Calcd. for $C_4H_5F_2N_3O_2$: C, 29.10; H, 3.05; N, 25.45; F, 23.02. Found: C, 28.80; H, 3.15; N, 25.36; F, 23.15.

Example 2

2-AZIDO-2,2-DIFLUOROETHANOL

To a solution of 0.42 g (11 mmol) of sodium borohydride in 20 mL of water at 5° C. was added 1.65 g (10.0 mmol) of ethyl 2-azido-2,2-difluoroacetate. The addition was accompanied by gas evolution. The homogeneous solution was stirred overnight at 20° C. Dilute hydrochloric acid (10 mL, 0.1M) was added to lower the pH to 2.5. The orange-yellow solution changed to a light yellow. Sodium chloride (8 g) was added and the solution was extracted with methylene chloride (3×10 mL). The dried ($Na_2SO_4$) extract was concentrated by distillation to a residue of 1.00 g, composed of 0.71 g 2-azido-2,2-difluoroethanol (58%) and 0.29 g $CH_2Cl_2$ by $^1H$ NMR analysis. A small amount of ethanol was removed by treatment with 4A molecular sieves. In a larger scale reduction experiment, the crude 2-azido-2,2-fluoroethanol was first treated with 4A sieves and then distilled. The pure alcohol had bp 73°–74° C./107–109 mm; $^{19}F$ NMR (neat) $\phi$86.3 (t, J=10.7 Hz), $CFCl_3$ ref.; $^1H$ NMR (neat) 3.83 (t, J=10.5 Hz), 4.63 (s).

Example 3

PHENYLURETHANE DERIVATIVE OF 2-AZIDO-2,2-DIFLUOROETHANOL

A solution of 1.18 g (9.56 mmol) 2-azido-2,2-difluoroethanol, 1.40 g (11.8 mmol) of phenylisocyanate, and 0.02 g of dibutyltin dilaurate was refluxed overnight. The $^{19}F$ NMR analysis indicated 96% reaction. The urethane was purified by column chromatography (Silica Gel) to give 2.54 g (73%) of N-phenyl 2-azido-2,2-difluoroethylcarbamate as a colorless liquid: $^{19}F$ NMR ($CDCl_3$) $\phi$83.3 (t, J=9.9 Hz); $^1H$ NMR ($CDCl_3$) 4.53 (t, J=10.0 Hz), 7.03 (s, NH) 7.53 (m); IR (film) 3360 (N-H), 2180 ($N_3$), and 1755 (C=O) $cm^{-1}$. Anal. Calcd. for $C_9H_8F_2N_4O_2$: C, 44.63; H, 3.33; F, 15.69; N, 23.14. Found: C, 44.68; H, 3.42; F, 15.85; N, 23.35.

Obviously, numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. 2-azido-2,2-difluoroethanol.

* * * * *